US005783214A

United States Patent [19]
Royer

[11] Patent Number: 5,783,214
[45] Date of Patent: Jul. 21, 1998

[54] BIO-ERODIBLE MATRIX FOR THE CONTROLLED RELEASE OF MEDICINALS

[75] Inventor: Garfield P. Royer, Cashtown, Pa.

[73] Assignee: Buford Biomedical, Inc., Cashtown, Pa.

[21] Appl. No.: 258,672

[22] Filed: Jun. 13, 1994

[51] Int. Cl.[6] .............................. A61K 9/14; A61K 9/50; A61K 37/22; A61E 2/00
[52] U.S. Cl. .................... 424/499; 424/422; 424/423; 424/425; 424/426; 424/451; 424/457; 424/464; 424/468; 424/484; 424/488; 424/489; 424/490; 424/491; 424/492; 424/493
[58] Field of Search ...................... 424/484, 451, 424/488, 457, 492, 464, 499, 468, 422, 491, 423, 489, 425, 490, 493, 426

[56] References Cited

U.S. PATENT DOCUMENTS

| | | | |
|---|---|---|---|
| 3,925,344 | 12/1975 | Mazur | 260/112.5 |
| 4,064,118 | 12/1977 | Wong | 260/112.5 |
| 4,349,530 | 9/1982 | Royer | 424/426 |
| 4,983,393 | 1/1991 | Cohen et al. | 424/430 |
| 5,041,292 | 8/1991 | Feijen | 424/484 |
| 5,122,367 | 6/1992 | Ron et al. | 514/2 |
| 5,271,961 | 12/1993 | Mathiowitz et al. | 427/213.31 |
| 5,308,620 | 5/1994 | Yen | 424/484 |

FOREIGN PATENT DOCUMENTS

WO 91/06287  5/1991  WIPO .
WO 93/25221 12/1993 WIPO .

OTHER PUBLICATIONS

Joung, J.J., et al, Reprinted from Biochemical Engineering VI, vol. 589 of the *Annals of the New York Academy of Sciences*, May 20, 1990 "Immobilization of Growing Cells and Its Application to the Continuous Ethanol Fermentation Process", p. 271–282.

Means, G.E., Chemical Modification, "Reductive Alkylation of Amino Groups", p. 469–478.

Royer, G.P., et al, Reprinted from Journal of Parenteral Science and Technology, Mar./Apr. 1983, "Entrapment of Bioactive Compounds within Native Albumin Beads", p. 34–37.

Lee, T.K., et al. Science, Reprint Series 10 Jul. 1981, vol. 213, pp. 233–235, "Serum Albumin Beads: An Injectable, Biodegradable System for the Sustained Release of Drugs."

Golumbek, P.T., et al, Cancer Research 53, 5841–5844 Dec. 15, 1993 "Controlled Release, Biodegradable Cytokine Depots: A New Approach in Cancer Vaccine Design".

Gref, R., et al, Science, vol. 263, 18 Mar. 1994 "Biodegradable Long–Circulating Polymeric Nanospheres".

*Primary Examiner*—Frederick Krass
*Attorney, Agent, or Firm*—Nixon & Vanderhye P.C.

[57] ABSTRACT

A bioerodible matrix for the controlled release of medicinals including protein therapeutics is disclosed. A method for controlled drug release is also disclosed.

28 Claims, 7 Drawing Sheets

BIO-ERODIBLE MATRIX FOR THE CONTROLLED RELEASE OF MEDICINALS

FIELD OF THE INVENTION

This invention relates generally to a bio-erodible delivery system which enables timed release of medicinals including proteins and small molecules.

BACKGROUND OF THE INVENTION

The rapid progress in recombinant DNA technology has provided researchers and clinicians with a variety of newly discovered proteins in amounts sufficient to enable laboratory and clinical study (*Cytokines*, A. Meager, Prentis Hall, 1991). Proteins either currently being administered by physicians or under investigation include growth factors, interferons, colony stimulating factors, and interleukins. In nature these molecules may act locally as paracrine agents; i.e., they interact with and activate nearby cells. Further, they can be pleiotropic, i.e., they can activate or stimulate more than one kind of cell.

Delivery of these highly potent molecules for treatment of disease remains a challenge. Serious toxicity, low maximum tolerated doses (MTD), and limited therapeutic windows have been observed. As noted above, since some of these molecules are paracrine agents, localized delivery is another issue (Golumbek, P. T., et al, *Cancer Research*, 53, 5341 (1993)). As an example, systemic use of certain colony stimulating factors may result in autoimmunity and tissue damage from intense inflammatory reactions. Temporary relief of illness may be followed by permanent damage to the immune system.

Many novel proteins now being investigated for clinical use have very short half-lives. Clearance from the circulation can occur in a few hours or even a few minutes. Hence, prolonged release of effective doses below the MTD would be advantageous.

Recombinant hormones such as BGH are widely used in dairy cattle. BGH is currently administered biweekly by injection. Controlled release of protein components in veterinary vaccines is desirable. Reduction of the frequency of injection and improvement in performance of the bioactive protein would be advantageous.

Bio-erodible polymers have been used for encapsulation of numerous classes of drugs (U.S. Pat. No. 4,349,530; Royer, G. P., et al, *J. Parenteral Science & Technol.*, 37, 34 (1983); Lee, T. K., et al, *Science*, 213, 233 (1981); WO91/06287 (1991); WO93/25221 (1993), all of which are hereby incorporated by reference). Synthetic polymers and copolymers of lactic acid and glycolic acid have been extensively investigated (U.S. Pat. No. 5,122,367; Langer, *Science*, 249, 1927 (1990); U.S. Pat. No. 4,983,393 (1991)). Autologous albumin and gelatin are also exemplified in the literature (U.S. Pat. No. 4,349,530; Royer, G. P., et al, *J. Parenteral Science & Technol.*, 37, 34 (1983); Lee, T. K., et al, *Science*, 213, 233 (1981)). Cross-linking with glutaraldehyde is known to stabilize albumin and gelatin matrices. Glutaraldehyde, however, is non-specific in its reaction with proteins. As a result, the protein drug can be inactivated or covalently bound to the matrix components. The latter reaction lowers the effective amount of deliverable drug or creates an antigenic molecule. A negative consequence of the latter chemical reaction is the development of autoimmunity.

U.S. Pat. No. 4,349,530 discloses implants, microbeads and microcapsules comprising cross-linked but physically-native albumin and a biologically active substance. The implants, microbeads and microcapsules may contain an inactive form of a protease capable of dissolving albumin.

U.S. Pat. No. 4,983,393 discloses a composition for use as an intra-vaginal insert comprising agarose, agar, saline solution glycosaminoglycans, collagen, fibrin and an enzyme.

Failures of conventional delivery systems for proteins are typically attributable to lack of design for controlled release, denaturation of the protein in the matrix, adverse immunological reactions, or chemical modification of the medicinal during formulation.

OBJECTS OF THE INVENTION

It is an object of the invention to provide a bioerodible delivery system which enables timed release of medicinals.

It is an object of the invention to provide a delivery system for proteins which does not alter the biological activity of the proteins.

It is a further object of the invention to provide a delivery system where the release profile is easily altered.

SUMMARY OF THE INVENTION

The subject invention relates to a medicinal delivery system comprising (i) at least one protein selected from the group consisting of gelatin and albumin, (ii) a polymeric stabilizer and/or an external cross-linker, and optionally (iii) an enzyme capable of degrading said protein or said polymeric stabilizer, wherein said system is stabilized by said protein being crosslinked with said polymeric stabilizer and/or said external cross-linker.

The invention also includes a sustained release delivery system comprising (a) a first gel matrix comprising (i) a protein selected from the group consisting of gelatin and albumin, and (i) a polymeric stabilizer and/or an external cross-linker, and (iii) a medicinal protein wherein said first gel matrix is stabilized by said protein being cross-linked to said polymeric stabilizer and/or said external cross-linker, and (b) a second gel matrix comprising (i) a protein selected from the group consisting of gelatin and albumin, and (ii) a polymeric stabilizer and/or an external cross-linker, and (iii) an enzyme capable of degrading said protein or said polymeric stabilizer, wherein said second gel matrix is stabilized by said protein being cross-linked to said polymeric stabilizer and/or said external cross-linker.

Also provided by the invention is a medicinal delivery system comprising (i) at least one matrix protein selected from the group consisting of gelatin and albumin, and (ii) a polymeric stabilizer and/or an external cross-linker, wherein said system is stabilized by said protein being crosslinked with said polymeric stabilizer and/or said external cross-linker, and (iii) an enzyme capable of degrading said protein or said polymeric stabilizer embedded on the surface of said system.

Delivery systems of the invention for sustained release comprise at least two gel matrices wherein at least two of said gel matrices have different levels of cross-linking (internal or external), gel density and/or enzyme.

The invention also includes a method for obtaining sustained release of a medicinal comprising administering the delivery systems of the invention to a mammal.

Additionally, the invention includes a method of synthesizing a drug delivery system comprising the steps of mixing matrix protein, protected medicinal protein, hydrolytic enzyme, and polymeric stabilizer and shaping the mixture into a gel matrix, and optionally curing said gel matrix with an external crosslinker.

DETAILED DESCRIPTION OF THE INVENTION

Figure 1:
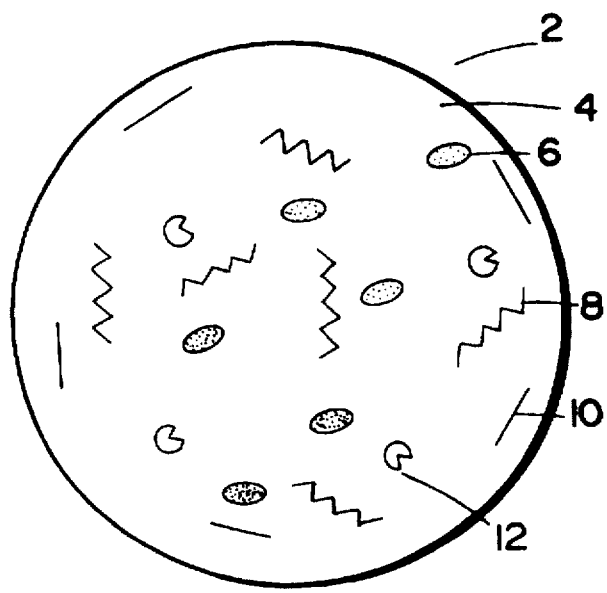
FIG. 1 is a schematic representation of a gel matrix for the timed release of proteins (gelatin molecules not shown)

The present invention relates to a biopolymer gel matrix 2 designed for the controlled release of medicinals 6 including proteins and small molecules. The hydrophilic, non-immunogenic gel matrix consists of (i) one or more proteins, such as gelatin (collagen) and/or albumin 4, (ii) a polymeric stabilizer 8 such as a polysaccharide or polynucleotide and/or an external cross-linker 10 and optionally (iii) an enzyme 12. The matrix protein concentration (gel density), the composition of the matrix protein 4, the concentration of medicinal 6, the shape and size of the gel matrix 2, the amount of polymeric stabilizer 8, the degree of external cross-linking 10 and the amount of enzyme are adjusted to achieve the desired release profile.

Many proteins denature at hydrocarbon-water interfaces. Indeed, to stabilize sensitive proteins often requires inclusion of an "inert" protein such as albumin. Gelatin (collagen) is commonly used to pre-treat surfaces which inactivate or adsorb proteins. Gelatin and albumin are readily available and have very low antigenic potential. Stable dosage forms can be made at moderate temperatures and near neutral pH.

Various types of collagen may be used as the matrix protein 4 in the subject invention, e.g., types A and B, Bloom Nos. 60–300. Advantageously, human collagen is used for human administration.

In addition to gelatin, other non-immunogenic matrix proteins can be used in the subject invention. Serum albumin can be used especially when a strong gel is desired. Human, bovine and rabbit serum albumin may be used. Advantageously, the albumin is native to the animal into which the gel matrix is to be administered. Available amino groups in the form of lysine are high in number in serum albumin. Lysine constitutes approximately 13% of the amino acid composition of serum albumin.

In one embodiment both gelatin and serum albumin are used together as the matrix protein. The ratio of these two components can vary, for example 50:50 (w/w), 60:40, 70:30, 80:20 or 90:10 with either protein being present as the primary component.

Elastin, hemoglobin, myoglobin and proteins of basement membrane can also be used as the matrix protein 4.

The gel matrix 2 can be formed as beads, granules, implants, microspheres (100–200 microns), threads, cylinders, disks, films or cell-sized microspheres (less than 100 microns) using techniques presented herein and known to those skilled in the art. The gel matrix 2 is typically stabilized internally by cross-linking with the polymeric stabilizer 8, either through ionic bonds, or covalent bonds when the polymeric stabilizer 8 carries amine specific functional groups such as aldehydes and imidates. The gel matrix is optionally stabilized by an external cross-linker 10 such as a multi-functional imidate.

It is useful to stabilize protein gels with covalent cross-links. In solution glutaraldehyde exists in polymeric forms which contain sites for Michael addition reactions with thiols, amines, phenolic hydroxyls, etc. (see Table 1).

TABLE 1

Reactivities of functional groups in proteins.

| Functional Group | Acylimidazole | Glutaraldehyde | Diazonium Salts | CHO/NaBH4 | Imidates |
|---|---|---|---|---|---|
| —NH₂ | + | + | + | + | + |
| —SH | + | + | + | − | − |
| 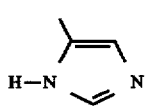 | + | + | + | − | − |
| 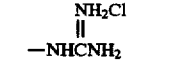 | − | − | + | − | − |
| 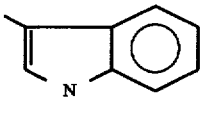 | − | − | + | − | − |
| —CO₂H | − | ? | − | − | − |
| +S—S— | − | − | − | − | − |

In the present invention, polyfunctional amine-specific aldehydic and amidination reagents are used to stabilize the matrix in preference to glutaraldehyde which is non-specific (see Table 1).

Gel Matrix Preparation

Figure 2:
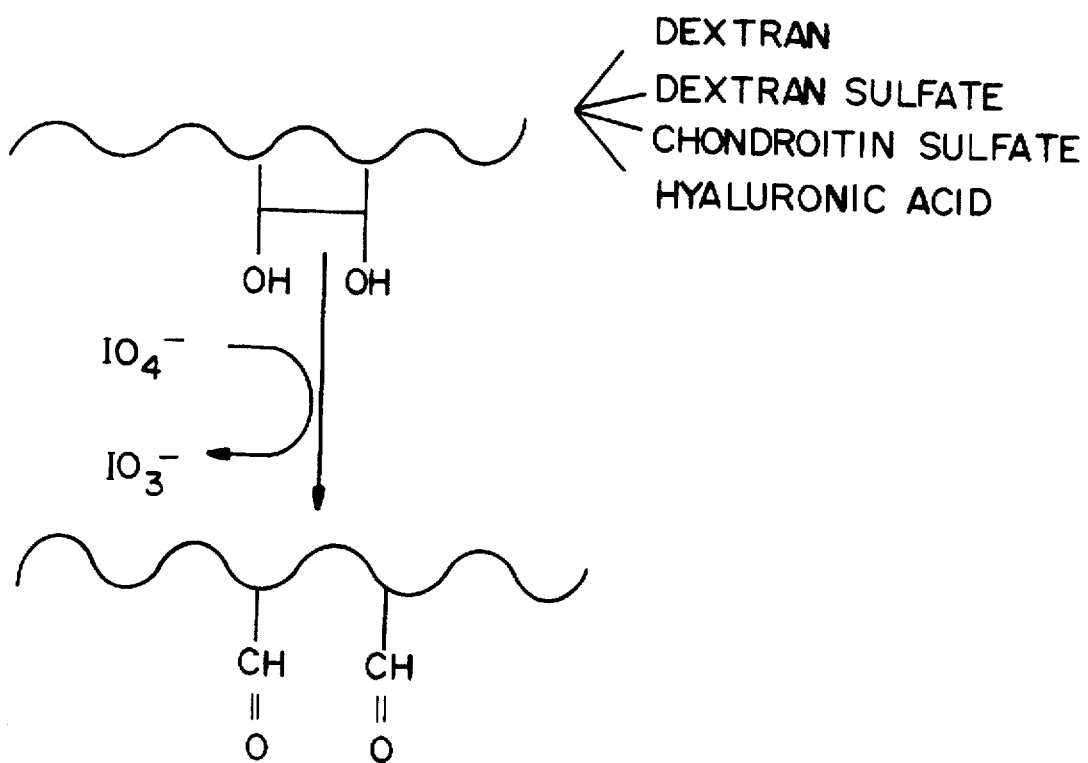
FIG. 2 shows periodate oxidation of polysaccharides.

Advantageously, the gel matrix 2 components include a matrix protein 4, a polymeric stabilizer 8, a hydrolytic enzyme 12, and an external cross-linker 10. The gel matrix 2 is schematically represented in FIG. 1. Gelatin (or other matrix protein) molecules, which are in excess, are not specifically shown. The matrix preparation typically occurs in three steps:

1. The medicinal is mixed with the matrix components (e.g., matrix protein, polymeric stabilizer and enzyme). The medicinal is dissolved or dispersed as an amorphous or crystalline solid. The polymeric stabilizer is optionally included in the formulation prior to gelation. One approach involves formation of a gelatin-polysaccharide bead in a rapidly stirred dispersion in a water-immiscible substance. The anionic polysaccharide can be activated by pre-treatment with sodium m-periodate (FIG. 2). The resulting polyfunctional dialdehyde reacts to form primarily internal cross-links.
2. The gel matrix is formed into the desired shape (beads, cylinders, disks, etc.).
3. The solidified matrix is optionally subjected to an external cross-linker to provide added stability and to prolong release. Multivalent metal cations and/or chemical cross-linkers can be added to cure the outside of the gel matrix. The frequency of chemical cross-links near the outside of the gel is a result of diffusing the bifunctional reagent into a previously formed gel matrix ("curing").

Polymeric Stabilizers

Polysaccharides, such as those listed in the first column of Table 2 are useful as polymeric stabilizers in the gel matrix of the subject invention.

TABLE 2

| Amine specific cross-linking reagents. | |
| --- | --- |
| Polymeric Stabilizers (Internal Cross-linkers) | External cross-linkers |
| Dialdehyde-dextran | Imidates |
| Dialdehyde-dextransulfate | $\underset{\text{MeO}-\text{C}-\text{R}-\text{C}-\text{OMC}}{\overset{NH_2Cl \quad NH_2Cl}{\| \quad \quad \|}}$ |
| Dialdehyde-Chondroitin Sulfate Dialdehyde-Hyaluronic Acid | $R = (CH_2)_n$ or $(CH_2CH_2O)_n$ |

Chondroitin sulfate and hyaluronic acid are immunologically inert. Strong gels can be formed using polyanions such as polysaccharides in combination with multivalent metal ions and polymeric cations (Joung, J. J., et al, *Appl. Biochem. Biotechnol.*, 14, 259 (1987)). In addition to chondroitin sulfate and hyaluronic acid, dextran (including oxidized dextran, i.e., dextran-CHO) and dextran sulfate have been used successfully. Clinical grade dextran has the advantages of low cost and ease of handling. Polynucleotides are also useful as polymeric stabilizers.

The degree of internal cross-linking can be varied. The rate of release is inversely related to the degree of cross-linking.

External Cross-linkers

Once the gel matrix is formed into the desired shape, treatment with an external cross-linker (i.e., curing the gel matrix) is desirable where added physical stability and prolonged release are needed. For example, beads prepared either in water or in organic medium, can be subjected to curing by soaking the beads in a solution of diimidate. The rate of release is inversely related to the degree of external cross-linking.

Advantageously, amine-specific cross-linkers are used in the subject invention. Diimidates form stable amidine adducts with amino groups of proteins and are especially useful as external cross-linkers. Advantageous compounds useful as external cross-linkers are presented in the second column of Table 2.

For delivery of non-proteinaceous drugs, other less specific cross-linkers are also useful. Examples include: multifunctional alkylating agents, multifunctional acylating agents, and multifunctional carbonates such as

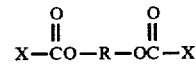

in which X is a leaving group such as a halide, a phenol or hydroxy succinimide. If a hydrolytic enzyme is to be included, it must be pre-treated with an analogous monofunctional reagent to avoid covalent immobilization within the matrix. An example of the latter reagent is acetyl imidazole.

In one embodiment of the invention, only an external cross-linker is used, i.e., polymeric stabilizer is omitted.

\* \* \*

Sub-batches of beads (or other shapes) can be prepared by cross-linking (either using internal or external cross-linkers) for varying time periods. For example, beads can be made where 10, 20, 30, 40, 50, 60, 70, 80 or 90 percent of available amino groups are subject to cross-linking. These sub-batches can be used to constitute blends of beads. To illustrate, when these blends of beads contain proportionately more of the heavily cross-linked sub-batch, the release is relatively slow. Blends of beads weighted toward lightly cross-linked sub-batches release drug relatively quickly.

Enzymes

Programmable erosion of the gel matrix (and timed release of the medicinal) is made possible in the present invention by including one or more hydrolytic enzymes in the gel matrix. As an example, when beads are chosen as the gel form, the hydrolytic enzyme can be included directly into the proteinaceous bead containing the drug, in companion beads, or added to the formulation as free enzyme.

Conditions for the preparation and storage of gel matrix must be selected to avoid enzymatic degradation prior to use. It is well known that enzyme activity is strongly dependent on pH, temperature, ionic strength, and the presence of modifiers. Conditions such as low temperature and pH can be selected to suppress enzyme activity. Lyophilization can also be used to suppress enzyme activity.

Figure 6:
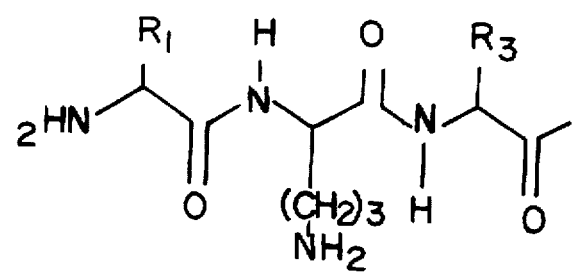
FIG. 6 presents schemes for the modification of amino groups in therapeutic proteins and enzymes.
Figure 6:
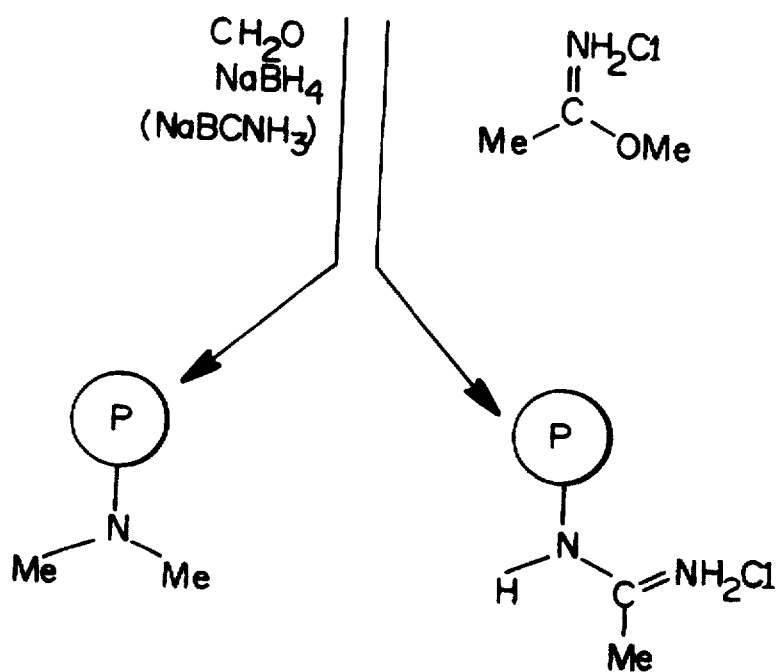

Enzymes may react with the cross-linker in a manner similar to the medicinal protein, and should therefore be protected. It is well known that amino groups of enzymes can be modified without loss of activity. Therefore, pretreatment of the enzyme according to methods described below with respect to the medicinal proteins (see FIG. 6) may be carried out on enzymes prior to direct incorporation.

Figure 3A:
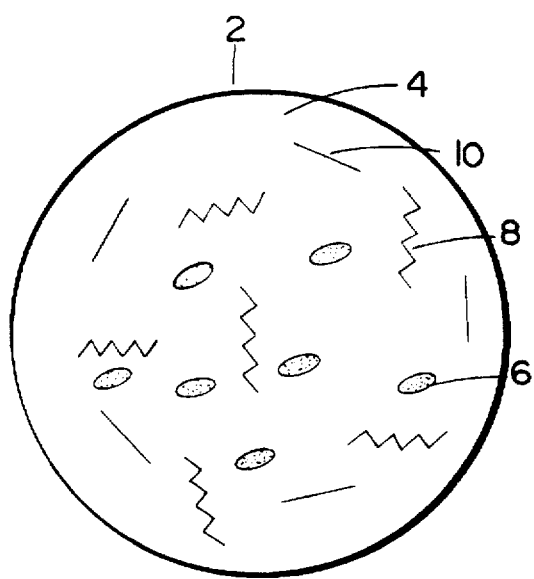
FIGS. 3A and B show companion beads containing hydrolytic enzyme.
Figure 3B:
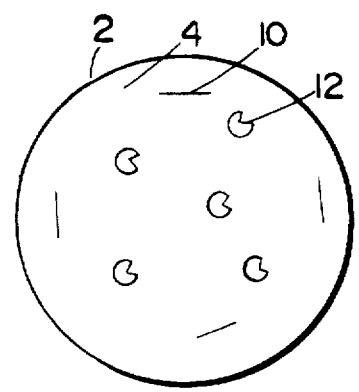

In a second embodiment, the hydrolytic enzymes 12 are included in companion gel matrix beads 2 as shown in FIG. 3B. In this case the population of the drug-containing gel matrix beads 2 is homogeneous. The enzyme 12 containing beads 2 are blended to achieve the desired release profile. Companion beads 2 with high enzyme content and low degree of cross-linking would produce fast release. In contrast, companion beads 2 with low enzyme content and high degree of cross-linking would result in slow release.

Figure 4:
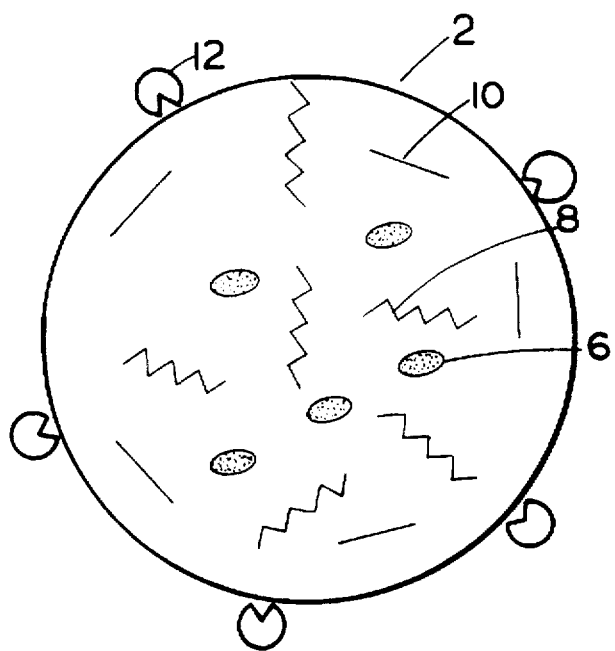
FIG. 4 shows an externally catalyzed erosion of protein beads.

In a third embodiment, hydrolytic enzymes 12 are added directly to the formulation in soluble or in crystalline form (see FIG. 4). Gel matrix beads 2 and enzyme 12 are mixed just prior to administration or stored together in the dosage form under conditions which do not support enzyme activity such as low ionic strength, low pH, or absence of activators. In a variation of this embodiment enzymes are also present in the gel matrix.

Figure 5:
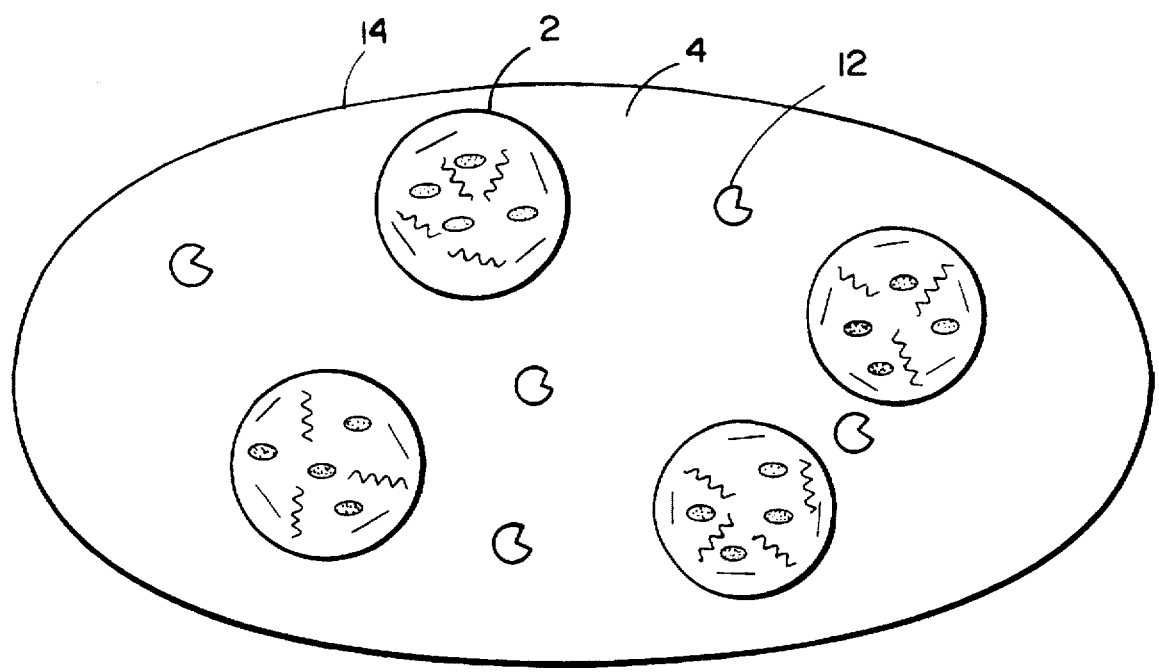
FIG. 5 shows an implant or capsule for oral delivery.

In a fourth embodiment of the invention, an implant or capsule 14 is constructed as shown in FIG. 5. A blend of gel matrix beads 2 with varying amounts of cross-linking is included in the advantageously low density gel capsule or implant 14. Prolonged release is achieved by weighting the blend in favor of highly cross-linked gel matrix beads 2. Also, collagenase (enzyme containing) beads 2 can be included to modulate release rate. The implant or capsule 14 may have a semipermeable membrane (for use as an implant) or enteric coating (for oral use).

An advantageous enzyme is collagenase, which digests the gelatin matrix component. Alternatively, an enzyme specific for the polymeric stabilizer is used. Hyaluronidase, dextranase, or nuclease represent this latter type of enzyme.

Digestion of the gel matrix has two results—reduction of the viscosity of the medium through which the protein medicinal must travel and perforation of the gel matrix surface. The hydrolytic enzymes must have narrow specificities which exclude the medicinal protein.

Purified collagenase selectively cleaves after X in the sequence PRO-X-GLY-PRO where X is any neutral amino acid. PRO can designate either proline or hydroxyproline. GLY represents glycine. Although very frequent in collagen, the sequence, PRO-X-GLY-PRO is generally rare in proteins.

Hyaluronidase cleaves glycoseaminoglyeans but not polypeptides. It catalyzes the hydrolysis of glycosidic bonds of beta-N-acetyl-hexosamine (1,4-linked).

Gels containing relatively high amounts of hydrolytic enzymes will permit faster release of the medicinal. Desired delivery profiles can be produced by blending batches of beads with varying amounts of enzyme. In one embodiment more than one type of enzyme is included in the gel matrix, e.g., dextranase and collagenase.

Medicinal Proteins

As used herein the term medicinals includes proteins as well as small molecule agents. The term "protein" includes naturally occurring proteins, recombinant proteins, protein derivatives and polypeptides. Medicinal proteins useful in the subject invention include colony stimulating factors (CSF) including G-CSF, GM-CSF, and M-CSF; erythropoietin; interleukins, IL-2, IL-4, IL-6, etc; interferons; growth factors (GF) including epidermal-GF, nerve-GF; tumor necrosis factor (TNF); hormones/bioactive peptides; ACTH; angiotensin, atrial natrincetic peptides, bradykynin, dynorphins/endorphins/β-lipotropin fragments, enkephalin; gastrointestinal peptides including gastrin and glucacon; growth hormone and growth hormone releasing factors; luteinizing hormone and releasing hormone; melanocyte stimulating hormone; neurotensin; opiode peptides; oxytocin, vasopressin and vasotocin; somatostatin; substance P; clotting factors such as Factor VIII; thrombolytic factors such as TPA and streptokinase; enzymes used for "replacement therapy," e.g., glucocerebrosidase, hexoseaminidase A; and antigens used in preventative and therapeutic vaccines such as tetanus toxoid and diptheria toxoid.

Protection of the Medicinal Proteins

In order to avoid chemical cross-linking of the medicinal protein within the matrix, prior to exposing the therapeutic protein to the cross-linking reagent, the bioactive protein is modified to deactivate functional groups which would normally react with the cross-linking agent, i.e., the protein is "protected." In the case of certain proteins, there is no need to modify the protein for it to be protected and useful in the subject invention, e.g., a protein where amino groups are not available. Since the cross-linkers of choice attack primary amino groups, these groups are protected in the medicinal protein. For example, the protein is first rendered unreactive to amine-directed reagents by treatment with formaldehyde and a reducing agent, or by other suitable reagents, such as methyl acetimidate. The charge, structure and biological activity of the reductively alkylated protein is not significantly changed but the procedure prevents further reaction with aldehydes or other reactions such as acylation or amidination.

Reductive methylation and amidination are examples of appropriate reactions for amino group protection. These treatments are known to have minimal effect on biological activity probably because of the minor structural change and similar net charge of the reactant and product at neutral pH (Means, G. E., *Methods Enzymol.*, 47, 469 (1977)). Both techniques are convenient and give consistent results. Antigenicity of the reductively methylated proteins is not enhanced over native structures.

Other methods of amino group protection include (i) acylation, (ii) lycosylation and (iii) carbamylation.

Examples of acylation reactions are:
1. acetylation
2. maleylation
3. citraconylation
4. trifluoroacetylation
5. acetoacetylation
6. ethoxyformylation Examples of glycosyl groups include:
1. glucosyl
2. lactosyl
3. galactosyl
4. mannosyl
5. maltosyl
6. fructosyl
7. arabinosyl
8. fucosyl
9. combinations of the above Carbamylation reactions are also appropriate for amino group protection:

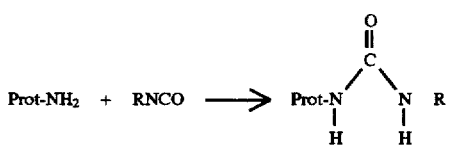

R can be hydrogen, in which case the reactant is cyanate and the product is a substituted urea.

There are numerous other amino group modifications known to those skilled in the art such as guanidination and sulfonylation. Non-specific alkylating reagents are to be avoided. However, where stable derivative favor amine adducts, this class of reagents may be useful.

Examples of protected medicinal proteins are dimethylated and amidinated derivatives of the proteins listed above under "Medicinal Proteins", e.g., dimethylated G-CSF or dimethylated IL-2. It should be noted that the lysines in some proteins are not available for reaction due to location. There is no need for these locations to be protected since the same locations are inaccessible to cross-linking.

Non-Protein Delivery

Although especially well suited for parenteral administration of proteins, the present delivery system is also applicable to formulations with non-protein medicinals, including but not limited to alkaloids, steroids, terpenoids, amino acid derivatives, nucleoside/nucleotide derivatives, polynucleotides, carbohydrates, polysaccharides, lipids, lipopolysaccharides, purines, pyrimidines and derivatives of same.

Advantageous small molecule drugs include: analgesics, anesthetics, antialcohol preparations, anti-infectives, anticoagulants, anticancer drugs, antidepressants, antidiabetic agents, antihypertensive drugs, antiinflammatory agents, antinauseants, anorexics, antiulcer drugs, cardiovascular drugs, contraceptives, decongestants, diuretics, hormones/antihormones, immunosuppressives, narcotic detoxification agents, uncosuric agents, agrichemicals such as pheromones, wood protection chemicals and wound healing promoters.

Particularly advantageous compounds for use in the subject invention are those in crystalline form.

Films for transdermal delivery or for topical application as bandages can also be formed. In this case the film may be used to deliver non-proteinaceous drugs such as anti-infectives and wound healing promoters.

* * *

Typical delivery systems are shown in Table 3:

TABLE 3

| Matrix Protein[1] | Polymeric Stabilizer | Hydrolytic Enzyme[2] | External Cross-Linker |
|---|---|---|---|
| G = 100% A = 0 | Dextran-CHO | Collagenase | DMS[3] |
| G = 100% A = 0 | Chondroitin sulfate | Collagenase | DMS |
| G = 100% A = 0 | Chondroitin sulfate | Hyaluronidase | DMS |
| G = 50% A = 50% | Dextran-CHO | Collagenase | DMS |
| G = 50% A = 50% | Dextran-CHO | Hyaluronidase | DMS |
| G = 25% A = 75% | Dextran-CHO | Dextranase | — |
| G = 25% A = 75% | Chondroitin sulfate | Hyaluronidase | DMS |
| G = 50% A = 50% | Polynucleotide | Nuclease | DMS |
| G = 50% A = 50% | — | Collagenase | DMS |
| G = 50% A = 50% | Dextran-CHO | Collagenase | — |

Figure 7:
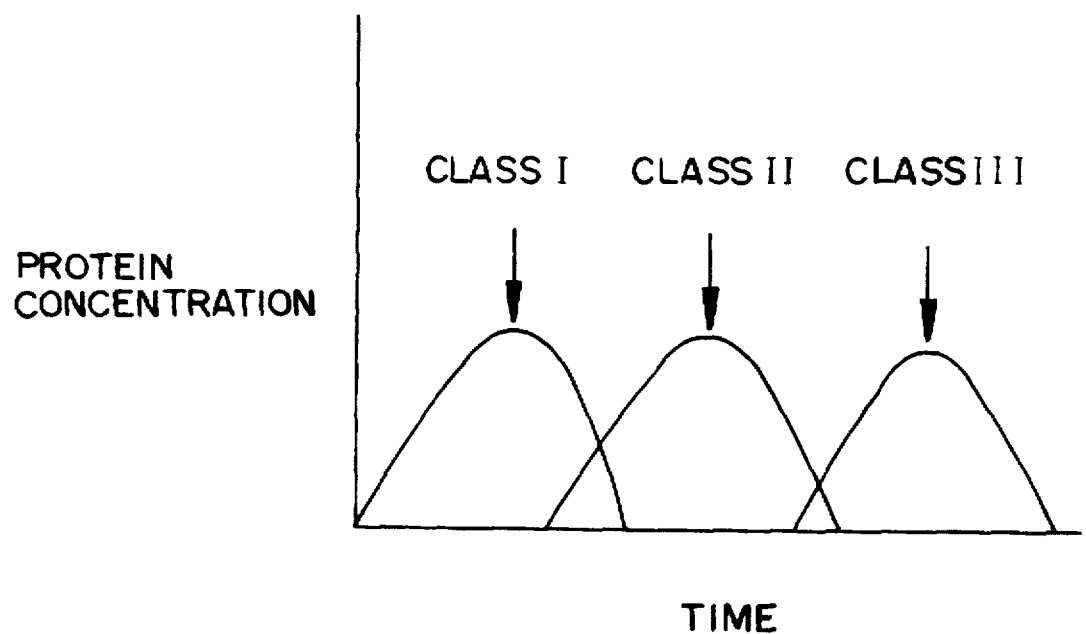
FIG. 7 is an idealized profile of programmed release: Class I—contains high levels of enzyme and low matrix density and cross-linking; Class II—moderate enzyme concentration, density, and degree of cross-linking; Class III—low enzyme concentration and in a highly cross-linked, dense matrix.

[1] G = gelatin (collagen) and A = albumin
[2] Delivered either by the same matrix (internal) or by a different matrix (external)
[3] Dimethyl Suberimidate Timed Release of Medicinals and Modes of Administration An idealized release profile is shown in FIG. 7. Here the concentration of medicinal in the vicinity of the bead reflects the rate of internal degradation of the three different classes of gel matrices. The profile shown depicts the system with identical medicinal concentration in all classes. For example, to have higher levels of medicinal released at a later period, more medicinal would be incorporated in the Class III beads as shown in this example.

Release profiles can be obtained from zero order release to those involving late-stage bursts.

It is also possible to administer more than one medicinal in the same treatment regimen. The drugs could be released simultaneously or sequentially.

Stokes law is applicable, i.e., $$D \propto 1/rv$$

The diffusion coefficient (D) is inversely related to the radius of the protein (r) and the viscosity of the medium (v), which is dependent on the density and degree of cross-linking of the gel matrix. Computer modelling of this system with four to seven adjustable parameters can be used to generate a set of hypothetical release profiles for a given therapeutic protein.

Medicinal matrix of the invention is administered to a human or other mammal as beads, disks, threads and implants of various other shapes using techniques known to those skilled in the art. Beads would be normally administered via needle subcutaneously, intramuscularly, intraperitoneally, or intravenously for cell-sized microbeads. Tablets and capsules are used for oral delivery.

Medicinal matrix can be administered concomitant with surgical procedures. An example would be antibiotic matrix following abdominal surgery. Also, implants can be surgically placed under the skin or elsewhere.

* * *

The following Examples are illustrative, but not limiting of the compositions and methods of the present invention. Other suitable modifications and adaptations of a variety of conditions and parameters normally encountered in clinical therapy which are obvious to those skilled in the art are within the spirit and scope of this invention.

EXAMPLES

Example 1
Production of Protected Proteins for Use in the Delivery Systems

Reductive methylation of the protein is carried out with formaldehyde and sodium borohydride at 0°–4° C. in 0.2M borate buffer, pH 9. In cases where lower pH is required, sodium cyanoborohydride is used in place of sodium borohydride at pH values below pH 9. The protein concentration is 1–10 mg/ml. The borohydride is added in advance of the formaldehyde with moderate stirring. For each milliliter of protein solution, 0.5 mg borohydride is added followed by 2.5 microliters of formaldehyde solution (37%) in five increments at five minute intervals. The procedure is repeated if necessary. The modified protein is purified by dialysis or gel filtration.

Example 2
Preparation of Activated Polysaccharide

Generation of dialdehydes from diols by using periodate oxidation is accomplished as follows. The reaction is carried out in the pH range of 4.5–6.5. A polysaccharide, such as chondroitin sulfate, hyaluronic acid, dextran, dextran sulfate, or the like, is dissolved in distilled water (0.1–10 mg/ml). An equal volume of sodium metaperiodate solution (1–50 mM) is added and the mixture is maintained at room temperature in the dark for about an hour. Higher temperature and longer reaction time result in more extensive oxidation. The activated polymer is purified by dialysis, gel filtration or ultrafiltration.

Example 3
Preparation of Molded Gels Containing Bioactive Proteins

Many different shapes are possible because of the reaction dynamics and their control. A cylindrical implant is conveniently made by using a plastic syringe. The syringe is filled with reaction mixture which is then allowed to set. The constricted end is cut off and the plunger is depressed to expel the gel cylinder.

A reaction mixture is as follows: Solution I—Type A gelatin (0.5–5 g) is dissolved in hot Hepes buffer (50 ml, 10 mM pH 7–8.5) and then cooled to 37° C. Solution II—to an activated polysaccharide solution (0.05–1% in 10 mM Hepes, pH 7–8.5) is added the protected protein (and enzyme if included in the formulation). Protected protein concentration is in the range of 10–2000 micrograms/ml and the protected hydrolytic enzyme concentration is in the range of 1–50 micrograms/ml. The reaction mixture is composed of equal volumes of Solution I (gelatin) and Solution II (polymeric stabilizer) described above. The two solutions are mixed with a dispo pipette and loaded into the syringe. The gelation occurs at room temperature in 2–5 hr. The cylinder is forced out in one piece or incrementally forced out and cut into disks of desired thickness. These cylinders or disks are optionally further stabilized by soaking in a solution containing an amine specific cross-linking reagent such as dimethylsuberimidate (10 mM Hepes, 1–100 mM imidate, 1–5 hr). The surface curing reaction is terminated by pouring off the imidate solution and quenching with 0.1M aminoethanol-HCl, pH 8.5 for 1 hour.

Example 3A
Films

The procedure of Example 3 is repeated using other geometric configurations including films containing antibiotics and wound healing promotors. The reaction mixture is poured onto a flat glass plate with borders to provide boundaries of the desired dimensions. The glass plate is cooled to −20° C. and allowed to stand for 4–8 hours.

Example 4
Formation of Microbeads in a Non-miscible Solvent

For formation of microbeads, the Hepes buffer contains 0.1% sodium dodecyl sulfate, and the reaction mixture (as above) is injected into a rapidly stirring hydrocarbon phase (corn oil:petroleum ether-4:1, 100 ml, 0°–4° C.). After an hour, the beads are harvested, washed with petroleum ether, and surface cured as described above. The resulting beads are about 100 microns in diameter.

Example 4A
Beads Containing Dispersed Solid Medicinal

The procedure of Example 4 is repeated but with 10–40% by weight of a crystalline or amorphous solid medicinal suspended in the reaction mixture.

Example 5
Microsphere Formation in Water

The basic gelatin stock solution (5 ml) is mixed with activated polysaccharide with rapid stirring. The concentration of activated polysaccharide is in the range of 0.1–1%. The protected protein is included in the original solution of the activated polysaccharide within the concentration range of 1–5000 micrograms/ml. These microspheres are collected by centrifugation and surface cured as described above.

Example 6
Controlled Release of Azoalbumin from Three Preparations

Controlled release was demonstrated using three preparations made as disks (2×6 mm in diameter) according to Example 3. Class I contained mildly oxidized dextran and was not treated with external cross-linkers; Class II contained intermediate levels of dextran-dialdehyde and was externally cross-linked for thirty minutes with an intermediate concentration of dimethylsuberimidate (DMS). Class III contained the maximum activated polysaccharide and was soaked in 0.1M DMS for five hours. Each preparation contained Type A gelatin/Bloom # 60/1.5% final concentration and 2% protected azoalbumin. All were treated with 200 micrograms of collagenase in one ml of Tris buffer (10 mM, pH 7.4, 1 mM $CaCl_2$). The results are shown in Table 4.

TABLE 4

| | Class I | Class II | Class III |
|---|---|---|---|
| Halftime of albumin release | <5 min | 2 wks | negligible release over 1 month |

It will be readily apparent to those skilled in the art that numerous modifications and additions may be made to both the present invention, the disclosed device, and the related system without departing from the invention disclosed.

What is claimed is:
1. A gel matrix medicinal delivery system comprising
   (i) at least one matrix protein selected from the group consisting of gelatin and albumin,
   (ii) a protected medicinal protein,
   (iii) an amine specific polymeric stabilizer and/or an amine specific external cross-linker, and optionally
   (iv) an enzyme capable of degrading said protein or said polymeric stabilizer, wherein said system is stabilized by said matrix protein being crosslinked with said polymeric stabilizer and/or said external cross-linker.
2. A gel matrix medicinal delivery system comprising
   (i) at least one matrix protein selected from the group consisting of gelatin and albumin,
   (ii) an amine specific polymeric stabilizer selected from the group consisting of oxidized dextran, dialdehyde-dextran sulfate, dialdehyde-chondroitin sulfate, and dialdehyde-hyaluronic acid, and optionally
   (iii) an enzyme capable of degrading said protein or said polymeric stabilizer, wherein said system is stabilized by said matrix protein being crosslinked with said polymeric stabilizer.
3. A system as in claim 1 wherein said polymeric stabilizer is selected from the group consisting of dialdehyde-dextran, dialdehyde-dextransulfate, dialdehyde-chondroitin sulfate, and dialdehyde-hyaluronic acid.
4. A system as in claim 1 wherein said external cross-linker is a diimidate selected from the group consisting of dimethyl suberimidate, pimelimidate, dimethyladipimidate and suberic acid bis(N-hydroxy succinimide).
5. A system as in claim 1 or claim 2 wherein said matrix protein is albumin, and said polymeric stabilizer is oxidized dextran.
6. A system as in claim 1 or claim 2 wherein said matrix protein is gelatin, and said polymeric stabilizer is oxidized dextran.
7. A system as in claim 1 or claim 2 wherein said matrix protein is a mixture of gelatin and albumin, and said polymeric stabilizer is oxidized dextran.
8. A system as in claim 1 or claim 2 wherein said matrix protein is a mixture of gelatin and albumin, and said polymeric stabilizer is dialdehyde chondroitin sulfate.
9. A system as in claim 1 or claim 2 wherein said polymeric stabilizer is oxidized dextran.
10. A system as in claim 1 or 2 wherein said system is in the form of a bead.
11. A system as in claim 1 or 2 wherein component (i) comprises 0–80% by weight albumin and 0–80% by weight gelatin.

12. A system as in claim 1 or 2 wherein less than 20% of the available gelatin and/or albumin amino groups are cross-linked.

13. A sustained release delivery system comprising:
（a) a first gel matrix comprising
   (i) a matrix protein selected from the group consisting of gelatin and albumi, and
   (ii) an amine specific polymeric stabilizer and/or an amine specific external cross-linker, and
   (iii) a protected medicinal protein
wherein said first gel matrix is stabilized by said matrix protein being cross-linked to said polymeric stabilizer and/or said external cross-linker, and
(b) a second gel matrix comprising
   (i) a matrix protein selected from the group consisting of gelatin and albumin, and
   (ii) an amine specific polymeric stabilizer and/or an amine specific external cross-linker, and
   (iii) an enzyme capable of degrading said matrix protein or said polymeric stabilizer.
wherein said second gel matrix is stabilized by said matrix protein being cross-linked to said polymeric stabilizer and/or said external cross-linker.

14. A medicinal delivery system comprising
(i) at least one matrix protein selected from the group consisting of gelatin and albumin, and
(ii) an amine specific polymeric stabilizer and/or an amine specific external cross-linker,
wherein said system is stabilized by said matrix protein being crosslinked with said polymeric stabilizer and/or said external cross-linker,
(iii) an enzyme capable of degrading said matrix protein or said polymeric stabilizer embedded on the surface of said system and
(iv) a protected medicinal protein.

15. A delivery system as in claim 13 wherein said enzyme and medicinal protein are protected.

16. A blend of gel matrices for sustained release comprising at least two gel matrices according to claim 1 or 2 wherein at least two of said gel matrices have different levels of internal cross-linking.

17. A blend of gel matrices for sustained release comprising at least two gel matrices according to claim 1 or 2 wherein at least two of said gel matrices have different levels of external cross-linking.

18. A blend of gel matrices for sustained release comprising at least two gel matrices according to claim 1 or 2 wherein at least two of said gel matrices have different levels of enzyme.

19. A blend of gel matrices for sustained release comprising at least two gel matrices according to claim 1 or 2 wherein at least two of said gel matrices have different levels of gel density.

20. A method for obtaining sustained release of a medicinal protein comprising administering the system of claim 1 to a mammal.

21. A method for obtaining sustained release of a medicinal protein comprising administering the system of claim 16 to a mammal.

22. A method as in claim 20 wherein said administration is oral.

23. A method of synthesizing a drug delivery system comprising the steps of:
   a) mixing a matrix protein selected from the group consisting of gelatin and albumin, protected medicinal protein, hydrolytic enzyme, and an amine specific polymeric stabilizer to form a gel matrix,
   b) shaping said gel matrix, and optionally
   c) curing said gel matrix with an external crosslinker.

24. A system as in claim 1 or claim 2 further comprising a compound selected from the group consisting of dextran, hyaluronic acid, chondroitin sulfate, dextran sulfate and polynucleotides.

25. A system as in claim 2 further comprising a therapeutic agent.

26. A system as in claim 25 wherein said therapeutic agent is an anesthetic or antiinflammatory.

27. A method of synthesizing a drug delivery system comprising the steps of:
   a) mixing matrix protein selected from the group consisting of gelatin and albumin, therapeutic agent, and polymeric stabilizer selected from the group consisting of oxidized dextran, dialdehyde-dextran sulfate, dialdehyde-chondroitin sulfate, and dialdehyde-hyaluronic acid, and optionally a hydrolytic enzyme, to form a gel matrix,
   b) shaping said gel matrix, and optionally
   c) curing said gel matrix with an external crosslinker.

28. A system as in claim 1 wherein said medicinal protein is in crystalline form.

* * * * *